United States Patent [19]

Hartman et al.

[11] 4,002,730

[45] Jan. 11, 1977

[54] RADIONUCLIDE CARRIERS

[75] Inventors: Frederick Anthony Hartman; Herbert Charles Kretschmar; Andrew John Tofe, all of Cincinnati, Ohio

[73] Assignee: The Procter & Gamble Company, Cincinnati, Ohio

[22] Filed: Jan. 13, 1975

[21] Appl. No.: 540,488

[52] U.S. Cl. .................... 424/1; 252/301.1 R; 536/45
[51] Int. Cl.² ............... A61K 29/00; A61K 43/00; G01T 1/161
[58] Field of Search ............ 424/1, 288, 294, 295; 252/301.1 R; 260/233.3 R, 233.5

[56] References Cited

UNITED STATES PATENTS

| | | | |
|---|---|---|---|
| 2,400,287 | 5/1946 | Caesar | 260/233.5 R X |
| 2,609,368 | 9/1952 | Gaver | 260/233.5 R X |
| 3,663,685 | 5/1972 | Evans | 424/1 |

*Primary Examiner*—Benjamin R. Padgett
*Assistant Examiner*—Christine M. Nucker
*Attorney, Agent, or Firm*—Jerry J. Yetter; Julius P. Filcik; Richard C. Witte

[57] ABSTRACT

Physiologically acceptable particulate radionuclide carriers comprising a reducing agent bound to an anionic starch derivative, useful in the preparation of organ-specific diagnostic radiopharmaceuticals.

11 Claims, No Drawings

RADIONUCLIDE CARRIERS

BACKGROUND OF THE INVENTION

This invention relates to scintigraphic scanning, and more particularly to organ-specific carriers for technetium-99m.

For some time it has been recognized that conventional organ scanning techniques are not entirely satisfactory for imaging specific body organs. The deficiencies of prior techniques have been generally attributed to the difficulty of preparing a stable radiolabeled diagnostic agent which can be safely delivered to a specific target organ.

In efforts to overcome these deficiencies, a variety of radionuclides have been examined for use as diagnostic agents. Recent interest has been directed toward the use of technetium-99m ($^{99m}Tc$) as the preferred radiolabel for diagnostic agents. $^{99m}Tc$ has been found to be a particularly desirable radionuclide due to its advantageous half-life of about six hours, its adaptability to existing imaging equipment, and its ready commercial availability. It is a general practice to utilize a stable pertechnetate ($^{99m}TcO_4^-$) complex, such as sodium pertechnetate, as a convenient source of $^{99m}Tc$. A $^{99m}TcO_4^-$ solution, in the oxidized pertechnetate form, is obtained, for example, from commercial generators by eluting them with an isotonic saline solution. However, $^{99m}Tc$ is unique among radionuclides in that as a radiolabel for diagnostic purposes it is generally useful only in its reduced form. Accordingly, carriers suitable for use with the $^{99m}Tc$ radionuclide must combine with or otherwise provide a reducing agent capable of reducing the pertechnetate ion to its lower valence state.

Recent efforts to provide efficacious radiodiagnostic carriers have been directed toward the use of critically sized particulate materials which, once labeled and administered, are selectively deposited in the specific target organ. For instance, it has been found that submicron particles, on the order of 0.5 to 1 micron, tend to accumulate in the liver while particles on the order of 10 to 100 microns tend to accumulate in the lungs; accordingly, submicron carriers have been used to selectively deliver gamma emitting radionuclides to the liver while larger carriers have been used to deliver radionuclides to the lungs.

In general, a suitable particulate carrier is one which can be easily prepared, is stable, has a narrow range of particle size, is readily radio-labeled, and easily metabolized or discharged by the target organ after diagnostic procedures are complete. Colloids, chelates, and macroaggregates of albumin or polysaccharides have been suggested as particulate radionuclide carriers. For example, U.S. Pat. No. 3,758,678, issued Sept. 11, 1973 to Lindsay, et al. described the preparation of spheroidal biodegradable polysaccharide carrier particles, having critical diameters, selected for their organ specificity.

Although such "sized" carriers provide a general improvement in radionuclide delivery, they are relatively difficult to prepare and are relatively unstable. It has been found that previously suggested particulate carries, when combined with a reduced radionuclide, such as a stannous-technetium complex, form undesirable colloidal aggregates of varying size which are deposited in non-target organs. Thus, the diagnostic accuracy of known particulate carriers is decreased by their combination with the preferred radionuclide. This decrease in accuracy not only reduces the efficacy of the scan, but also results in the exposure of uninvolved organs to radioactive materials.

SUMMARY OF THE INVENTION

The present invention provides physiologically acceptable particulate radionuclide carriers, especially adapted for use with oxidized radionuclides, comprising a modified anionic starch derivative bearing an average of from about 0.1% to about 1.5%, by weight, of a reducing agent.

DETAILED DESCRIPTION OF THE INVENTION

The particulate carriers of this invention comprise a modified physiologically acceptable anionic starch derivative which can be metabolized or otherwise degraded and readily discharged from the body.

Starches, which can be derivatized and modified as hereinafter detailed, suitable for use in the present invention include both natural and processed particulate starches such as dextrinated, hydrolyzed, oxidized, alkylated, hydroxyalkylated, acetylated, or fractionated starch (amylose and amylopectin). In addition, the starch may be of any origin, for example, corn starch, wheat starch, potato starch, rice starch, tapioca starch, and the like.

The particulate carriers of the present invention are prepared by a two step alteration of the basic starch particle. In the first step, an anionic starch derivative is prepared by introducing an average of from about 1% to about 20%, by weight, of anionic substituents into the molecular structure of the basic starch particle. In the second step, the anionic starch derivative of step one is bound to from about 0.1% to about 1.5%, by weight, of a reducing agent. It has been found that the degree of substitution (herein expressed as weight percent) of both the anionic and reducing agent substituents alters the efficacy of the carriers as a radiodiagnostic agent.

Anionic starch derivatives are well known in the art and can be prepared by various known methods. For example, the basic starch particle may be extracted using a hydrophilic lipid solvent, such as a lower alcohol, to remove any adhering fatty material and subsequently treated, under anhydrous conditions, with an inorganic acid or acid derivative containing the anion of choice. If desired, the resulting anionic starch derivative can be neutralized to prepare a starch derivative containing anions of the corresponding salts.

More specifically, illustrative anionic starch derivatives can be prepared by the following methods:

1. Starch nitrates can be prepared using nitrogen pentoxide and sodium fluoride in chloroform as described in U.S. Pat. No. 2,400,287 which is incorporated herein by reference;

2. Starch sulfates occur naturally in a variety of plants and animals and may be synthetically prepared using chlorosulfonic acid in pyridine or a sulfur-trioxide-pyridine complex. A general review of the methods of preparation of the inorganic esters, such as sulfates, of polysaccharides can be found in W. Pigman, and D. Horton, ed., *The Carbohydrates*, Vol. I.A, Chap. 8, Academic Press (2nd ed., 1972);

3. Phosphonate derivatives of starches are prepared by a displacement reaction using a phosphite and the halide or sulfonate derivative of the starch. This preparation is illustrated by the following reaction:

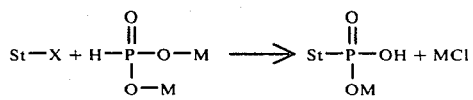

where M is an alkali metal and St-X is a chloro, bromo, iodo derivative of starch or a sulfonate, or arylsulfonate ester of a starch.

4. Starch alcoholates can be prepared by the method described in U.S. Pat. No. 2,609,368 incorporated herein by reference. The resulting alcoholate can be reacted with a halogen derivative of an alkylcarboxylate containing 1 to about 6 carbons, for example the alkali metal salt of chloroacetic acid, bromoacetic acid, 2-chloropropanoic acid, 3-chloropropanoic acid, 2-bromopropanoic acid, 3-bromopropanoic acid, 2-chlorobutanoic acid, 3-chlorobutanoic acid, 4-chlorobutanoic acid, 2-bromobutanoic acid, 3-bromobutanoic acid, 4-bromobutanoic acid, 2-chloro-2-methylpropanoic, 3-chloro-2-methylpropanoic acid, 2-bromo-2-methylpropanoic acid, 3-bromo-2-methylpropanoic acid, 2-chloropentanoic acid, 3-chloropentanoic acid, 4-chloropentanoic acid, 5-chloropentanoic acid, 2-bromopentanoic acid, 3-bromopentanoic acid, 4-bromopentanoic acid, 5-bromopentanoic acid, 2-chloro-2-methylbutanoic acid, 3-chloro-2-methylbutanoic acid, 4-chloro-2-methylbutanoic acid, 2-bromo-2-methylbutanoic acid, 3-bromo-2-methylbutanoic acid, 4-bromo-2-methylbutanoic acid, 3-chloro-2,2-dimethylpropanoic acid, and 3-bromo-2,2-dimethylpropanoic acid, to prepare a starch carboxylate. The overall reaction is illustrated by the following equation:

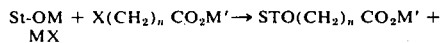

where St-OM is a starch and M and M' are alkali metals such as sodium potassium or lithium; $n$ can be any number from 1 to about 6;

5. Starch-alkylphosphonate compounds can be prepared by reacting a starch-alcoholate as prepared by U.S. Pat. No. 2,609,368 and incorporated by reference herein, with a haloalkylphosphonate. The haloalkylphosphonate is chosen from the chloro, bromo, or iodo derivatives of alkylphosphonates having 1 to about 6 carbon atoms. This reaction is illustrated by the following equation:

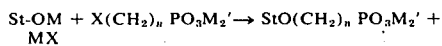

where St-OM is a starch alcoholate, X is a halogen, M and M' are alkali metals, and $n$ is an integer of 1 to about 6; and 6. Starch-alkyldiphosphonates may be prepared in the same manner as starch-alkylphosphonates described using a haloalkyldiphosphonate in place of a haloalkylphosphonate.

Introduction of the anionic substituents should be carried out in an essentially anhydrous state, to insure that the modified starch particles remain in an ungelatinized form, i.e., water-insoluble form. As described above, suitable physiologically acceptable anionic substituents include, for example, the anions of carboxylic, sulfonic, sulfuric, nitric, phosphoric, polyphosphonic, polyphosphoric, phosphonic, pyrophosphoric, and $C_1$ to $C_{10}$ alkylcarboxylic, alkylphosphoric, alkylpolyphosphonic, alkyl polyphosphoric, and alkyl phosphonic acids or the alkali metal (e.g., sodium and potassium), ammonium, or low molecular weight substituted ammonium (e.g., mono-, di-, and triethanolammonium) salts thereof. Preferred anionic substituents include the phosphoric acid, pyrophosphoric acid, phosphonic acid, polyphosphoric acid, and polyphosphonic acid anions. The most preferred anions include the pyrophosphate, ethyl-1-hydroxy-1,1-diphosphonate and phosphate anions. The phosphate anion is especially preferred.

In all cases it is essential that the anionic content of the starch derivative be adjusted so that the resultant particle remains substantially water-insoluble and biologically stable. Moreover, it has been found that anionic substituent content greater than about 20%, by weight, of the resulting anionic starch derivative causes the particle to swell and eventually disintegrate. Further, anionic substituent content of less than about 1%, by weight, has been found insufficient to insure binding of an adequate content of reducing agent, as hereinafter described. Accordingly, anionic substituents comprise an average of from about 1% to about 20%, preferably from about 3% to about 10%, by weight, of the anionic starch derivative.

Following derivatization, the resulting anionic starch derivative is modified by binding reducing agent substituents to the anionic starch structure. Binding is achieved by contacting the anionic derivative with an acid solution of a reducing agent. The term "reducing agent" in common usage and herein is intended to include substituents capable of donating electrons to an oxidized radionuclide source. For example, suitable reducing agents include the metallic stannous, ferrous, chromous and cuprous ions; other reducing agents, for example, hydrazines; bisulfite adducts; mercaptans; and sulfides, may also be bound to the anionic starch derivative. The metallic cations are preferred. The stannous ion is an especially preferred reducing agent.

As previously noted, the carriers of this invention are adapted for use with radionuclides which are utilized in their reduced valence state. It is therefore essential that the reducing agent, bound to the anionic starch derivative, be available in sufficient quantity to adequately reduce the radionuclide source, e.g., pertechnetate. It has been found that reducing agent content below an average of about 0.1%, by weight, is not sufficient to insure reduction of the radionuclide source. Moreover, it has been found that reducing agent content greater than about 1.5%, by weight, will result in the release of free substituents which form separate colloidal carriers capable of reducing and complexing with the radionuclide. Such colloidal carriers are free to transport the radionuclide to non-target organs and thus reduce the efficacy of the scan and unnecessarily expose non-target organs to radioactive materials. Accordingly, the reducing agent comprises an average of from about 0.1% to about 1.5%, preferably from about 0.2% to about 0.8%, by weight, of the carrier composition.

In use, the particulate carriers of the invention are pre-sized according to target organ selectivity and stored either as a dry powder or in isotonic saline solution. To form a radiolabeled diagnostic agent, the sized carriers are contacted with a radionuclide which is reduced and bound to the carrier particle. As noted technetium-99m is an especially preferred radionuclide.

As a radiolabeled diagnostic agent a quantity of the sized particles are parenterally administered to the patient for radiodiagnosis. The particles circulate throughout the body in the blood stream and, because of the selected particle size, will lodge in a particular predetermined organ. Radiation detectors may then be used to develop an image of the organ. Thereafter the particles are metabolized or otherwise degraded and are discharged from the body.

The following Example is intended to illustrate the invention.

EXAMPLE I

The preferred composition of this invention, a phosphorylated-starch-stannous composition containing from about 4% to about 5%, by weight, of phosphate and from about 0.2% to about 0.8%, by weight, of tin, was prepared as follows:

Removal of Lipids

The majority of lipids were removed from cornstarch employing a standard extraction technique. 200 Grams of cornstarch was mixed with 1.2 liters of chloroform, 400 ml methanol, and stirred at 26° C for 16 hours. The starch was allowed to settle and the liquid decanted. An additional 1 liter of methanol was added and the suspension was again stirred at 26° C at 16 hours. The starch was collected by suction filtration and washed 3 times with 1 liter portion of water followed by 3 washings with 1 liter portions of acetone. The starch cake was broken up and dried under vacuum (60°C/0.1 mm) for 16 hours. The isolated yield of defatted cornstarch was 162 grams (81%).

Phosphorylation

Phosphorylated cornstarch was prepared by the method described by Rolland Lohmann, et al., *Journal of the American Chemical Society*, 72, at page 5717 (1950), "Phosphorylation of Starch" (incorporated by reference herein). Following this procedure and employing cornstarch and 0.5 molar equivalent of phosphorus oxychloride, phosphorylated cornstarch containing 3½% phosphate anion was obtained in 97% yield.

Formation of Phosphorylated-Starch-Stannous Carrier

A solution of 16 ml. of concentrated hydrochloric acid containing 200 milligrams of stannous chloride dihydrate ($SnCl_2 \cdot 2H_2O$) was diluted to 200 ml. with deoxygenated water and mixed with 10 grams of phosphorylated starch. This suspension was stirred for 20 minutes, allowed to settle and the liquid decanted. An additional 400 ml. of 0.1N hydrochloric acid was added and the suspension stirred for 5 minutes. The starch was allowed to settle and the liquid decanted. This latter process was repeated. The modified starch derivative was mixed with 60 milliliters of acetone and collected by suction filtration. After air drying, final drying was under vacuum (0.1 mm) for 16 hours. The yield of dry particulate composition was 9.65 grams (94%).

Sizing to 10-45 Microns

The composition was ground in a mortar and pestle and sized through an ATM Sonic Sifter (ATM Corporation, Milwaukee, Wisconsin) employing precision sieves series L 3-M 45 (43-47 microns), L 3-M 30 (32-38 microns), L 3-M 20 (18-20 microns), L 3-M 10 (8-12 microns). Sizing was performed in 5 minutes employing amplitude settings 2 or 3, and amplitude pulse setting of 5. Sizing can also be performed manually using a Tyler Standard Screen 325 mesh (43 microns). In a case of phosphorylated cornstarch-stannous greater than 95% of the particles are 10-45 microns.

When contacted with potassium pertechnetate the sized carriers reduce and complex the technetium radionuclide thereby providing an efficacious radiolabeled radiodiagnostic agent.

The labeled carriers were parenterally administered to human patients, and were found to selectively lodge in the lungs thereby providing an efficacious radiodiagnostic agent.

Rice, wheat, potato, tapioca, sweet potato, arrowroot, canna, waxy maize, dasheen, and dextrinated starch are used in place of cornstarch in the foregoing preparation. The particle size of the phosphorylated starch varies with the source of the starch. Equivalent results were secured in that the sized particles when contacted with acid solutions of reducing agents form stable compositions which can be radiolabeled to form organ-specific radiodiagnostic agents.

In the above procedure, stannous chloride dihydrate is replaced by ferrous chloride, chromous chloride, stannous chloride, ferrous bromide, chromous bromide, and stannous bromide, respectively, and the corresponding starch phosphate composition is prepared.

In the above procedure, the phosphorylated starch is replaced by starch nitrate, starch sulfate, starch diphosphonate, starch carboxylate, starch ethylphosphonate, starch sodium propyldiphosphonate, and starch sulfonate and the corresponding anionic starch stannous composition is prepared.

What is claimed is:

1. A physiologically acceptable, substantially water-insoluble particulate radionuclide carrier comprising an anionic starch derivative comprising from about 1% to about 20% by weight anionic substituents, wherein an average of from about 0.1% to about 1.5%, by weight, of a reducing agent is bound to said starch derivative.

2. A radionuclide carrier according to claim 1, wherein the anionic substituent is a member selected from the group consisting of anions of phosphoric acid, phosphonic acid, pyrophosphoric acid, polyphosphoric acid, and polyphosphonic acid.

3. A radionuclide carrier according to claim 2, wherein said anionic substituent is the phosphate ion.

4. A radionuclide carrier according to claim 1, wherein said reducing agent is selected from the group consisting of the ferrous, cuprous, chromous, and stannous ions.

5. A radionuclide carrier according to claim 4, wherein said reducing agent is the stannous ion.

6. A radionuclide carrier according to claim 1 wherein the reducing agent is present in an amount of from about 0.2% to about 0.8% by weight.

7. A radiolabeled scintigraphic agent comprising a physiologically acceptable particulate water-insoluble radionuclide carrier comprising an average of from about 0.1% to about 1.5%, by weight, of a reducing agent bound to an anionic starch derivative having an average of from about 1% to about 20%, by weight, of anionic substituent, and a radionuclide.

8. A scintigraphic agent according to claim 7, wherein said radionuclide is technetium-99m.

9. A physiologically acceptable, substantially water-insoluble particulate radionuclide carrier according to claim 6 comprising from about 0.2% to about 0.8%, by weight, of stannous cation bound to an anionic starch derivative having an average of from about 4% to about 5%, by weight, of phosphate substituents.

10. A radiolabeled scintigraphic agent according to claim 8 wherein the radionuclide carrier comprises an anionic starch derivative which comprises phosphorylated starch containing from about 4% to about 5% by weight of phosphate substituents, and the reducing agent bound to said phosphorylated starch comprises from about 0.2% to about 0.8% by weight of tin.

11. A composition according to claim 10 wherein the radionuclide carrier has an average particle size in the range from about 10 microns to about 45 microns.

* * * * *